United States Patent
Banfi et al.

(10) Patent No.: US 7,091,382 B2
(45) Date of Patent: Aug. 15, 2006

(54) SYNTHESIS OF N-METHYL-N-PHENYLAMINOACROLEIN

(75) Inventors: Aldo Banfi, Milan (IT); Alfredo Mancini, Spinadesco (IT)

(73) Assignee: Clariant Life Science Molecules (Italia) S.p.A., Milan (IT)

(*) Notice: Subject to any disclaimer, the term of this patent is extended or adjusted under 35 U.S.C. 154(b) by 64 days.

(21) Appl. No.: 10/841,403

(22) Filed: May 7, 2004

(65) Prior Publication Data

US 2004/0229958 A1   Nov. 18, 2004

(30) Foreign Application Priority Data

May 13, 2003  (EP)  ................... 03425306

(51) Int. Cl.
  *C07C 211/00*  (2006.01)
(52) U.S. Cl. ...................... 564/345
(58) Field of Classification Search ................. 564/395
  See application file for complete search history.

(56) References Cited

U.S. PATENT DOCUMENTS 5,118,853 A   6/1992   Lee et al.

FOREIGN PATENT DOCUMENTS

GB            945 536        1/1964

OTHER PUBLICATIONS

George T. Lee et al., "Vinylformylation Utilizing Propeniminium Salts", Journal of Organic Chemistry, vol. 57, No. 11, 1992, pp. 3250-3252.

*Primary Examiner*—Samuel Barts
(74) *Attorney, Agent, or Firm*—Richard P. Silverman

(57) ABSTRACT

A process is disclosed for manufacturing N-methyl-N-phenylaminoacrolein of formula (I)

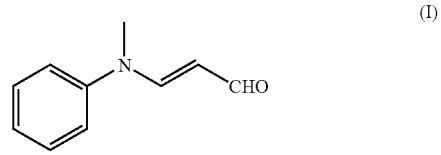

(I)

which comprises reacting N-methylformanilide and an alkyl vinyl ether of formula (III)

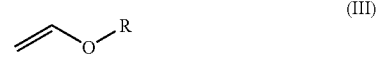

(III)

wherein R is a $C_3$–$C_4$ alkyl, said process being characterized in that the reaction between N-methylformanilide and said alkyl vinyl ether of formula (III) is carried out in the presence of phosgene, diphosgene or triphosgene in a solvent selected from dioxane, acetonitrile and/or chlorobenzene.

14 Claims, No Drawings

SYNTHESIS OF N-METHYL-N-PHENYLAMINOACROLEIN

This invention relates to the synthesis of N-methyl-N-phenylaminoacrolein of formula (I)

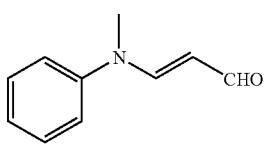

(I)

and its use for the preparation of 3-[3-(4-Fluorophenyl)-1-(1-Methylethyl)-1H-Indol-2-yl]-2-Propenal (II), hereinafter referred to as "Fenal",

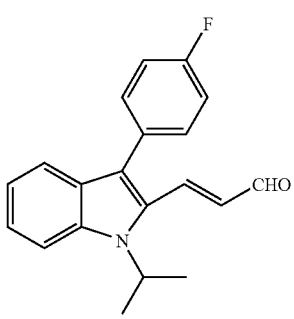

(II)

BACKGROUND OF THE INVENTION

Fenal is used as starting material for the preparation of compounds having HMG-CoA reductase inhibiting activity, such as Fluvastatin (CAS Registry number 93957-54-1), whose chemical formula is reported here-below:

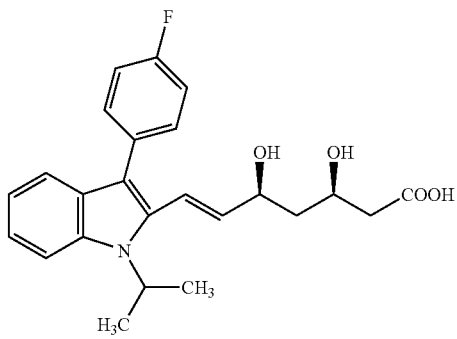

More in details, compound (I) can be converted into Fenal, by reaction with compound (IV)

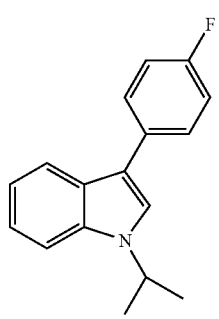

(IV)

in acetonitrile in the presence of $POCl_3$, as disclosed in WO 84/82131 and U.S. Pat. No. 4,739,073.

Methods for manufacturing (I) are for instance disclosed in J.O.C., 57, 3250–3252 (1992), GB-945536, and U.S. Pat. No. 5,118,853. More in details, the J.O.C.'s article discloses a method in which N-methylformanilide is reacted in dichloromethane with ethyl vinyl ether in the presence of $POCl_3$; GB-945536 discloses a method in which N-methylformanilide is reacted in dichloroethane with ethyl vinyl ether in the presence of phosgene; U.S. Pat. No. 5,118,853 discloses a method in which N-methylformanilide is reacted in dichloromethane with ethyl vinyl ether in the presence of oxalylchloride.

All the above methods are however characterized by the use of low boiling chlorinated solvents which, for well known safety reasons, are normally avoided in industrial processes. The purpose of the present invention is therefore that of finding an alternative method for manufacturing Fenal which is devoided of the drawbacks of the known methods and which may possibly afford higher yields.

DESCRIPTION OF THE INVENTION

According to the process of the present invention, (I) is obtained in one step by adding phosgene (1.0–1.3 equivalents) or diphosgene (0.5–0.65 equivalents) or triphosgene (0.34–0.43 equivalents) to a solution of N-methylformanilide (1 equivalent) and an alkyl vinyl ether of formula (III) (1 to 2 equivalents, preferably 1 equivalent)

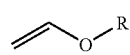

(III)

where R is a $C_3$–$C_4$ alkyl, preferably selected from ethyl, n-propyl, n-butyl, isobutyl, in a solvent selected from dioxane, acetonitrile and/or chlorobenzene; the reaction is carried out at a temperature of between 0° C. and 50° C., preferably at 15 to 25° C. (even more preferably at about 20° C.).

The reaction work-up can be carried out by adding an aqueous solution of alkaline hydroxide or alkaline carbonate to the reaction mixture in order to hydrolyse, in a biphasic system, the obtained intermediate and thus yield the desired acrolein (I). Alternatively, the solvent can be evaporated and the thus-obtained residue can be taken up with an aqueous solution of alkaline hydroxide or alkaline carbonate together with a solvent selected from tert-butyl methyl ether, chlorobenzene and/or toluene.

After separation of the phases, acrolein (I) is obtained as crude compound after evaporation to residue of the organic layer.

According to an embodiment of the invention the thus-obtained acrolein can be re-crystallised from tert-butyl methyl ether, hexane, heptane, cyclohexane, methanol, ethanol and/or isopropanol (tert-butyl methyl ether being the preferred) at a temperature of between −20° C. and 10° C. (preferably at about −15° C.).

However, the process of the present invention affords, after the hydrolysis, a crude N-methyl-N-phenylaminoacrolein (I) having such a high purity that the re-crystallisation is no longer necessary and which can be used without any further purification for the preparation of Fenal.

Therefore, in a preferred variant of the process, the crude (I) coming from the evaporation of the solvent is dissolved in acetonitrile and used for the preparation of Fenal (II) according to literature methods.

More preferably, in another variant of the described process, the crude mixture of the reaction of phosgene, diphosgene or triphosgene, N-methylformanilide and an alkyl vinyl ether of formula (III) in the claimed solvents is used without any purification for the "in situ" preparation of (II).

The following examples describe representative embodiments of the invention; however it should be understood that they are for purposes of illustration only.

EXAMPLE 1

N-methyl-N-phenylaminoacrolein

To a solution of N-methylformanilide (30 g), butyl vinyl ether (22.2 g) in 25 ml of 1,4-dioxane under stirring at 10–15° C., a solution of bis-trichloromethylcarbonate (28.3 g) in 50 ml of 1,4-dioxane is added dropwise in 90 min. The reaction mixture is kept under stirring at room temperature overnight, then the solvent is evaporated under reduced pressure. Tert-butyl methyl ether (75 ml) and water (55 ml) are added, the mixture is cooled at about 5–10° C. and the pH is corrected to about 7 by adding sodium hydroxide 30% aqueous solution (55 g). After separation of the phases, the aqueous layer is extracted with tert-butyl methyl ether (70 ml) and the combined organic layers are evaporated under reduced pressure. To the residue tert-butyl methyl ether (50 ml) is added and the mixture is cooled at −15° C. for 90 minutes. The precipitate is filtered on Buchner, washed twice with tert-butyl methyl ether (25 ml×2) and dried at room temperature under vacuum overnight. 25.21 g of pure compound are obtained (70% molar yield)

EXAMPLE 2

N-methyl-N-phenylaminoacrolein

To a solution of N-methylformanilide (30 g), butyl vinyl ether (22.2 g) in 25 ml of clorobenzene under stirring at 10° C., a solution of bis-trichloromethylcarbonate (24.3 g) in 50 ml of clorobenzene is added dropwise in 2 hours. The reaction mixture is kept under stirring at room temperature overnight. Water (50 ml) is added, the mixture is cooled at about 5–10° C. and the pH is corrected to about 7 by adding sodium hydroxide 30% aqueous solution (50 ml). After separation of the phases, the aqueous layer is extracted with chlorobenzene (50 ml) and the combined organic layers are washed with water (20 ml) and evaporated under reduced pressure. To the residue tert-butyl methyl ether (50 ml) is added and the mixture is cooled at −15° C. for 1 hour. The precipitate is filtered on Buchner, washed twice with tert-butyl methyl ether (25 ml×2) and dried at 30–35° C. under vacuum overnight. 24.66 g of pure compound are obtained (69% molar yield)

EXAMPLE 3A

N-methyl-N-phenylaminoacrolein

To a solution of N-methylformanilide (30 g), butyl vinyl ether (22.2 g) in 25 ml of 1,4-dioxane under stirring at 10–15° C., a solution of bis-trichloromethylcarbonate (28.3 g) in 50 ml of 1,4-dioxane is added dropwise in 90 min. The reaction mixture is kept under stirring at room temperature overnight, then the solvent is evaporated under reduced pressure. Toluene (50 ml) and water (200 ml) are added, the mixture is cooled at about 5–10° C. and the pH is corrected to about 7 by adding sodium hydroxide 15% aqueous solution (30 ml). After separation of the phases, the aqueous layer is extracted twice with toluene (50 ml×2) and the combined organic layers are washed with water (50 ml) and evaporated under reduced pressure. The obtained residue (32.3 g, containing, according to HPLC assay, 28.7 g of pure product, 81% molar yield) is used for the next step of the synthesis without any further purification.

EXAMPLE 3B

3-[3-(4-Fluorophenyl)-1-(1-Methylethyl)-1H-Indol-2-yl]-2-Propenal

Use of the crude acrolein coming from Example 3a. To a suspension of 3-[3-(4-Fluorophenyl)-1-(1-Methylethyl)-1H-Indole (35.8 g) phosphorus oxychloride (31.4 g) in acetonitrile (35 ml) cooled at 5° C. a solution of crude acrolein (32.3 g from Example 3a) in acetonitrile (40 ml) is added dropwise in 30 minutes. The reaction mixture is then warmed to 60° C. and kept under stirring at 60° C. for 4 hours; water (300 ml) is added and after 1 hour at 60° C. the formed solid is filtered on Buchner and washed with 75 ml of water. The wet solid (49.7 g) is dissolved in toluene (250 ml), celite (1 g) and charcoal (0.5 g) are added and the mixture is stirred at room temperature for 30 minutes. After filtration of the solid, the solvent is distilled off at reduced pressure and the residue is dissolved at 75° C. with isopropanol (72 ml). The solution is cooled at 20° C. and stirred at room temperature for 1 hour. The precipitate is filtered on Buchner, washed twice with isopropanol (15 ml) and dried at 60° C. under vacuum. 30.2 g (70% molar yield) of the product are obtained.

EXAMPLE 4A

N-methyl-N-phenylaminoacrolein

To a solution of N-methylformanilide (100 g), butyl vinyl ether (74.12 g) in 85 ml of clorobenzene under stirring at 5° C., a solution of bis-trichloromethylcarbonate (87.84 g) in 170 ml of clorobenzene is added dropwise in 2 hours. The reaction mixture is kept under stirring at room temperature overnight. The mixture is cooled at about 5° C. and the pH is corrected to about 7 by adding sodium hydroxide 15% aqueous solution (348 ml). After separation of the phases, the aqueous layer is extracted with chlorobenzene (90 ml) and the combined organic layers are washed with water (100 ml) and evaporated under reduced pressure. The obtained residue (116.9 g, containing, according to HPLC assay, 104.8 g of pure product, 88% molar yield) is used for the next step of the synthesis without any further purification.

EXAMPLE 4B

3-[3-(4-Fluorophenyl)-1-(1-Methylethyl)-1H-Indol-2-yl]-2-Propenal

Use of the crude acrolein coming from Example 4a. To a suspension of 3-[3-(4-Fluorophenyl)-1-(1-Methylethyl)-1H-Indole (130.7 g), phosphorus oxychloride (114.6 g) in acetonitrile (128 ml) cooled at 5° C. a solution of crude acrolein (116.9 g from Example 4a) in acetonitrile (145 ml) is added dropwise in 60 minutes. The reaction mixture is then warmed to 60° C. and kept under stirring at 60° C. for 6 hours; water (1100 ml) is added and after 1 hour at 60° C. the formed solid is filtered on Buchner and washed with water (250 ml×3). The wet solid (131 g) is dissolved in toluene (1050 ml), celite (2.7 g) and charcoal (4 g) are added and the mixture is stirred at room temperature for 30 minutes. After filtration of the solid, the mixture is washed with water (500 ml×2), the phases are separated, the organic solvent is distilled off at reduced pressure and the residue is dissolved at 75° C. with isopropanol (260 ml). The solution is cooled at 10° C. and stirred for 1 hour. The precipitate is filtered on Buchner, washed with isopropanol (60 ml×3) and dried at 60° C. under vacuum. 84.2 g (53% molar yield) of the product are obtained.

EXAMPLE 5

3-[3-(4-Fluorophenyl)-1-(1-Methylethyl)-1H-Indol-2-yl]-2-Propenal

To a solution of N-methylformanilide (30 g), butyl vinyl ether (22.2 g) in 15 ml of acetonitrile under stirring at 5° C., a solution of bis-trichloromethylcarbonate (26.1 g) in 70 ml of acetonitrile is added dropwise in 80 min. The reaction mixture is kept under stirring at 5° C. overnight, then phosphorus oxychloride (31.4 g) is added dropwise in 30 minutes, then the reaction mixture is stirred at 5° C. for 15 minutes. 3-[3-(4-Fluorophenyl)-1-(1-Methylethyl)-1H-Indole (35.8 g) and acetonitrile (25 ml) are added. The mixture is warmed to 80° C. and kept under stirring for about 24 hours. The reaction mixture is worked up as described in Example 3b to give the product (69% yield).

EXAMPLE 6

3-[3-(4-Fluorophenyl)-1-(1-Methylethyl)-1H-Indol-2-yl]-2-Propenal

The product is synthesised as described in Example 5 using chlorobenzene as solvent (70% yield).

What is claimed is:

1. A process for manufacturing N-methyl-N-phenylaminoacrolein of formula (I)

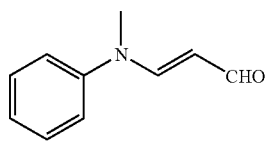
(I)

comprising the step of reacting N-methylformanilide and an alkyl vinyl ether of formula (III)

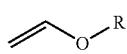
(III)

wherein R is a $C_3$–$C_4$ alkyl, wherein the reaction between said N-methylformanilide and said alkyl vinyl ether of formula (III) is carried out in the presence of triphosgene in a solvent selected from the group consisting of dioxane, acetonitrile chlorobenzene and mixtures thereof.

2. A process according to claim 1, wherein said solvent is chlorobenzene.

3. A process according to claim 1, wherein R is selected from the group consisting of ethyl, n-propyl, n-butyl, isobutyl and mixtures thereof.

4. A process according to claim 1, wherein the reaction is carried out at a temperature of 0 to 50° C.

5. A process according to claim 1, wherein the reaction is carried out at a temperature of 15 to 25° C.

6. A process according to claim 1, wherein the reacting step further comprises adding at least one of 1.0 to 1.3 equivalents of phosgene, 0.5 to 0.65 equivalents of diphosgene or 0.34 to 0.43 equivalents of triphosgene to an equimolar solution of N-methylformanilide and said alkyl vinyl ether of formula (III).

7. A process for manufacturing N-methyl-N-phenylaminoacrolein of formula (I)

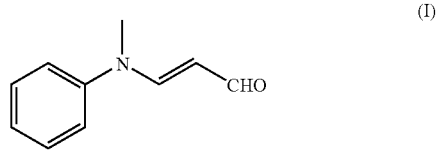
(I)

comprising the steps of reacting N-methylformanilide and an alkyl vinyl ether of formula (III)

(III)

wherein R is a $C_3$–$C_4$ alkyl, wherein the reaction between said N-methylformanilide and said alkyl vinyl ether of formula (III) is carried out in the presence of triphosgene in a solvent selected from the group consisting of dioxane, acetonitrile chlorobenzene and mixtures thereof
and an aqueous solution of alkaline hydroxide or carbonate to form an aqueous phase and at least one organic phase,
separating the aqueous phase from the at least one organic phase, and evaporating to residue of the at least one organic phase.

8. A process according to claim 1, further comprising
evaporating the solvent to form a residue and taking up the residue with an aqueous solution of alkaline hydroxide or carbonate and a solvent selected from the group consisting of tert-butyl methyl ether, chlorobenzene, toluene and mixtures thereof.

9. A process according to claim 7, further comprising the step of extracting the N-methyl-N-phenylaminoacrolein (I) from the aqueous phase with an ether.

10. A process according to claim 9, wherein said ether is tert-butyl methyl ether.

11. A process according to claim 9, further comprising the step of recrystallizing the N-methyl-N-phenylaminoacrolein (I) by adding at least one of tert-butyl methyl ether, hexane, heptane, cyclohexane, methanol, ethanol, isopropanol or mixtures thereof to the N-methyl-N-phenylaminoacrolein (I) at a temperature of between −20° C. and 0° C.

12. A process according to claim 1, wherein the reaction is carried out at a temperature of about 20° C.

13. A process according to claim 10, wherein tert-butyl methyl ether is used.

14. A process according to claim 10, wherein the recrystallization step occurs at a temperature of about −15° C.

* * * * *